(12) United States Patent
Meglan

(10) Patent No.: US 10,660,714 B2
(45) Date of Patent: May 26, 2020

(54) OPTICAL FORCE SENSOR FOR ROBOTIC SURGICAL SYSTEM

(71) Applicant: Covidien LP, Mansfield, MA (US)

(72) Inventor: Dwight Meglan, Westwood, MA (US)

(73) Assignee: COVIDIEN LP, Mansfield, MA (US)

( * ) Notice: Subject to any disclaimer, the term of this patent is extended or adjusted under 35 U.S.C. 154(b) by 222 days.

(21) Appl. No.: 15/768,342

(22) PCT Filed: Nov. 16, 2016

(86) PCT No.: PCT/US2016/062138
§ 371 (c)(1),
(2) Date: Apr. 13, 2018

(87) PCT Pub. No.: WO2017/087439
PCT Pub. Date: May 26, 2017

(65) Prior Publication Data
US 2018/0338803 A1 Nov. 29, 2018

Related U.S. Application Data

(60) Provisional application No. 62/257,564, filed on Nov. 19, 2015.

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00137* (2013.01); *A61B 34/37* (2016.02);
(Continued)

(58) Field of Classification Search
CPC ......... A61B 34/30; A61B 34/37; A61B 34/70; A61B 1/00137; A61B 2090/065;
(Continued)

(56) References Cited

U.S. PATENT DOCUMENTS

| | | | |
|---|---|---|---|
| 2006/0201262 A1* | 9/2006 | Hogeland | A61B 17/29 73/862.625 |
| 2009/0054908 A1* | 2/2009 | Zand | A61B 5/0071 606/130 |

(Continued)

FOREIGN PATENT DOCUMENTS

| | | |
|---|---|---|
| DE | 19523756 A1 | 1/1997 |
| WO | 2009079301 A1 | 6/2009 |

OTHER PUBLICATIONS

Extended European Search Report dated Jun. 17, 2019 corresponding to counterpart Patent Application EP 16866985.1.
International Search Report dated Mar. 2, 2017 in PCT/US16/062138.

*Primary Examiner* — Anh T Dang

(57) ABSTRACT

According to an aspect of the present disclosure, a surgical instrument is provided and includes a housing; an elongate shaft extending from the housing; and a tool assembly supported by a distal portion of the elongate shaft, the tool assembly including first and second jaw member. The at least one of the first and second jaw members is moveable relative to the other jaw member between a neutral configuration in which the first and second jaw members are spaced apart relative to one another; and a clamping configuration in which the first and second jaw members are approximated relative to one another with tissue grasped therebetween, the first jaw member defining a cavity.

20 Claims, 8 Drawing Sheets

(51) Int. Cl.
*G01L 1/25* (2006.01)
*A61B 34/37* (2016.01)
*A61B 34/00* (2016.01)
*A61B 90/00* (2016.01)

(52) U.S. Cl.
CPC ............... *G01L 1/25* (2013.01); *A61B 34/70* (2016.02); *A61B 2090/065* (2016.02)

(58) Field of Classification Search
CPC ............ A61B 17/29; A61B 17/320092; A61B 17/320068; A61B 18/1445; A61B 2017/2901; A61B 2017/2903; A61B 2017/2902; A61B 2017/2929; G01L 1/25
See application file for complete search history.

(56) References Cited

U.S. PATENT DOCUMENTS

| | | | | |
|---|---|---|---|---|
| 2010/0094163 A1* | 4/2010 | Deladi | ............... | A61B 5/02154 600/561 |
| 2011/0224687 A1* | 9/2011 | Larkin | ................ | B25J 19/025 606/130 |
| 2012/0265102 A1* | 10/2012 | Leo | ................ | A61B 90/06 600/587 |
| 2013/0190734 A1* | 7/2013 | Taylor | ................ | A61F 9/007 606/1 |
| 2014/0100588 A1* | 4/2014 | Blumenkranz | ........ | A61B 34/76 606/130 |

\* cited by examiner

OPTICAL FORCE SENSOR FOR ROBOTIC SURGICAL SYSTEM

CROSS-REFERENCE TO RELATED APPLICATIONS

This application is a U.S. National Stage Application filed under 35 U.S.C. § 371(a) of International Patent Application Serial No. PCT/US2016/062138, filed Nov. 16, 2016, which claims the benefit of and priority to U.S. Provisional Patent Application Ser. No. 62/257,564, filed Nov. 19, 2015, the entire disclosure of which is incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector that acts on a patient. The user interface includes an input controller that is moveable by the surgeon to control the robotic surgical system.

The robotic surgical system includes a surgical robot that is associated with the user interface. The surgical robot includes linkages that support a surgical instrument. The surgical instrument can include one or more jaw members that act on tissue of the patient during a surgical procedure. As the clinician manipulating the end effector is remote to the patient, it is important to accurately determine the forces exerted on the tissue by the jaw members.

Accordingly, there is a need for accurately determining forces exerted on or by the jaw members of the surgical instrument during a surgical procedure.

SUMMARY

This disclosure relates generally to optical force sensors that are disposed in one or more jaw members of a surgical instrument of a robotic surgical system. The optical force sensors directly measure the deflection of the respective jaw member in one or more directions to determine force exerted on or by the respective jaw member. The direct measurement of the deflection of the respective jaw member has been shown to provide an accurate measure of the force exerted on or by the respective jaw member.

The measured force can be used to provide feedback to a clinician engaged with the user interface of the robotic surgical system. In addition, the measured force can be used to enhance the function of a variety of instruments including, but not limited to, a grasper, a stapler (monolithic or two-part fasteners), electrosurgical forceps, and an endoscopic suturing device. For example, when the surgical instrument is a grasper, the measured force can be used to determine a force exerted on tissue by the grasper or to determine if an item (e.g., a suture) is slipping between two graspers. Additionally, when the instrument is a stapler, the measured force can be used to determine a force exerted to clamp tissue between the jaw members to prevent under or over clamping of the tissue before application of a one or two-part staple. Further, when the instrument is an electrosurgical forceps, the measured force can be used to optimize sealing, cutting, and/or coagulating of tissue between the jaw members. In addition, when the instrument is an endoscopic suturing device the measured force can be used to optimize the force exerted on a suture.

According to an aspect of the present disclosure, a surgical instrument is provided and includes a housing; an elongate shaft extending from the housing; and a tool assembly supported by a distal portion of the elongate shaft, the tool assembly including first and second jaw member. The at least one of the first and second jaw members is moveable relative to the other jaw member between a neutral configuration in which the first and second jaw members are spaced apart relative to one another; and a clamping configuration in which the first and second jaw members are approximated relative to one another with tissue grasped therebetween, the first jaw member defining a cavity.

The surgical instrument further includes an optical force sensor configured to determine a force exerted to tissue. The optical force sensor includes a light source; a reflector disposed within the cavity of the first jaw member and configured to reflect light emitted from the light source; a light receiver configured to sense an amount of light reflected from the light source; and a processor in communication with the light receiver and configured to determine deflection of the first jaw member from the amount of sensed light, the deflection of the first jaw member correlated to a force exerted by the first jaw member to tissue.

The light source may be disposed within the housing.

The optical force sensor may include a light guide extending between the light source and the cavity.

The light receiver may be disposed within the housing and in communication with the light guide such that light reflected from the reflector passes through the light guide.

In use, light reflected from the reflector may have at least one property different than light emitted towards the reflector, the at least one property is at least one of a phase or a wavelength.

The light receiver may be disposed within the cavity.

The first jaw member may have a tissue contacting surface opposing the second jaw member and an outer surface opposite the tissue contacting surface. The first and second jaw members may have a distracting configuration in which the outer surface of the first jaw member is engaged with tissue.

In the clamping configuration, the first jaw member may be deflected in a first direction, and in the distracting configuration, the first jaw member may be deflected in a second direction opposite the first direction. The processor may be configured to determine a direction of deflection of the first jaw member from the amount of light received by the light receiver.

The reflector may be disposed orthogonal to an axis of transmittance of light emitted from the light emitter.

The reflector may be disposed at an angle relative to an axis of transmittance of the light emitted from the light emitter in a range of about 5° to about 85°.

The reflector may be concave. The concavity of the reflector may be configured to direct the entire amount of light emitted from the light source towards the light detector when the first jaw member is in the neutral configuration.

The light source may be at least one of a microLED or a laser diode.

According to a further aspect of the present disclosure, a tool assembly is provided and includes a jaw member defining a cavity; and an optical force sensor configured to determine a force exerted to tissue by a jaw tool assembly, the tool assembly defining a cavity. The optical force sensor includes a first light source; a reflector disposed within a cavity of the tool assembly and configured to reflect light emitted from the first light source; a light receiver configured to sense an amount of emitted by the first light source and reflected by the reflector; and a processor in communication with the light receiver and configured to determine deflection of the first jaw member from the amount of sensed light, the deflection of the first jaw member correlated to a force exerted by the first jaw member to tissue.

The optical force sensor may include a second light source. The reflector may be configured to reflect light emitted from the second light source. The light receiver may be configured to sense an amount of light emitted by the second light source and reflected by the reflector.

The cavity may be defined by a first sidewall and a second sidewall perpendicular to the first sidewall. The first light source may be configured to emit light through an opening in the first sidewall and the second light source may be configured to emit light through an opening in the second sidewall.

The first light source may be configured to emit light having a first property and the second light source is configured to emit light having a second property different from the first property, the light detector differentiating between sensed light from the first light source and sensed light from the second light source.

According to still another aspect of the present disclosure, a method is provided for determining a force applied to tissue by a jaw member of a tool assembly. The method includes engaging tissue with a jaw member of a tool assembly such that the jaw member is deflected; emitting light from a light source towards a reflector disposed within a cavity defined in within the jaw member; sensing an amount of light from the first light source reflected by the reflector with a light detector; and determining the force applied to the tissue by the jaw member from the amount of sensed light.

The engaging tissue with the jaw member may include at least one of engaging tissue with a tissue contacting surface of the jaw member in a clamping configuration or engaging tissue with an outside surface of the jaw member opposite the tissue contacting surface in a distracting configuration.

The determining of the force applied to tissue by the jaw member may include a configuration of the jaw member based on the amount of sensed light.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
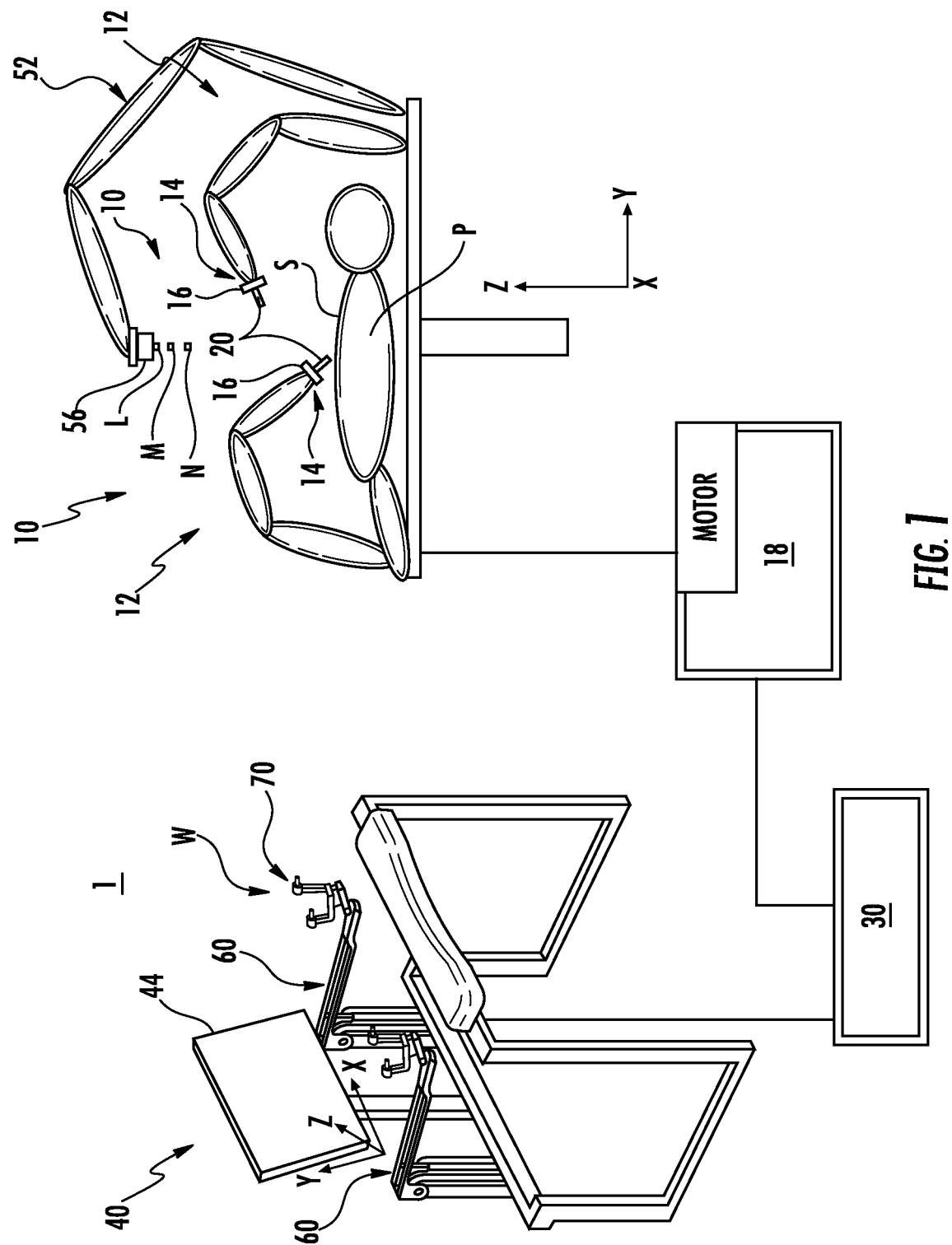
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to optical force sensors that are disposed in one or more jaw members of a surgical instrument of a robotic surgical system. The optical force sensors directly measure the deflection of the respective jaw member in one or more directions to determine force exerted on or by the respective jaw member. The optical force sensor includes a light source, a light guide, a reflector, and a light receiver. The light guide is in communication with the light source to transmit light produced by the light source into a cavity defined within a jaw member of the surgical instrument. An amount of the transmitted light is reflected off of the reflector and returned into the light guide. The light receiver measures an amount of light returned into the light guide to determine the deflection of the jaw member. The reflector is supported within the cavity such that as the jaw member is deflected, the amount of light returned into the light guide varies.

Referring to FIG. 1, a robotic surgical system 1 is shown generally as a robotic system 10, a processing unit 30, and a user interface 40. The robotic system 10 generally includes linkages 12 and a robot base 18. The linkages 12 moveably support an instrument 20 which is configured to act on tissue. The linkages 12 may be in the form of arms or links each having an end 14 that supports an instrument 20 which is configured to act on tissue. In addition, the ends 14 of the linkages 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging linkage 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input devices or handles attached to gimbals 70 which allow a clinician to manipulate the robotic system 10 (e.g., move the linkages 12, the ends 14 of the linkages 12, and/or the instruments 20). Each of the gimbals 70 is in communication with the processing unit 30 to transmit control signals thereto and to receive feedback signals therefrom. Additionally or alternatively, each of the gimbals 70 may include control interfaces or input devices (not shown) which allow the surgeon to manipulate (e.g., clamp, grasp, fire, open, close, rotate, thrust, slice, etc.) the instruments 20 supported at the ends 14 of the linkages 12.

Each of the gimbals 70 is moveable to move the ends 14 of the linkages 12 within a surgical site "5". The three-dimensional images on the display device 44 are orientated such that movement of the gimbals 70 moves the ends 14 of the linkages 12 as viewed on the display device 44. It will be appreciated that the orientation of the three-dimensional images on the display device may be mirrored or rotated relative to view from above the patient "P". In addition, it will be appreciated that the size of the three-dimensional images on the display device 44 may be scaled to be larger or smaller than the actual structures of the surgical site "S" permitting the surgeon to have a better view of structures within the surgical site "S". As the gimbal 70 is moved, the instruments 20 are moved within the surgical site "S". Movement of the instruments 20 may also include movement of the ends 14 of the linkages 12 which support the instruments 20.

For a detailed discussion of the construction and operation of a robotic surgical system 1, reference may be made to U.S. Pat. No. 8,828,023, the entire contents of which are incorporated herein by reference.

Figure 2:
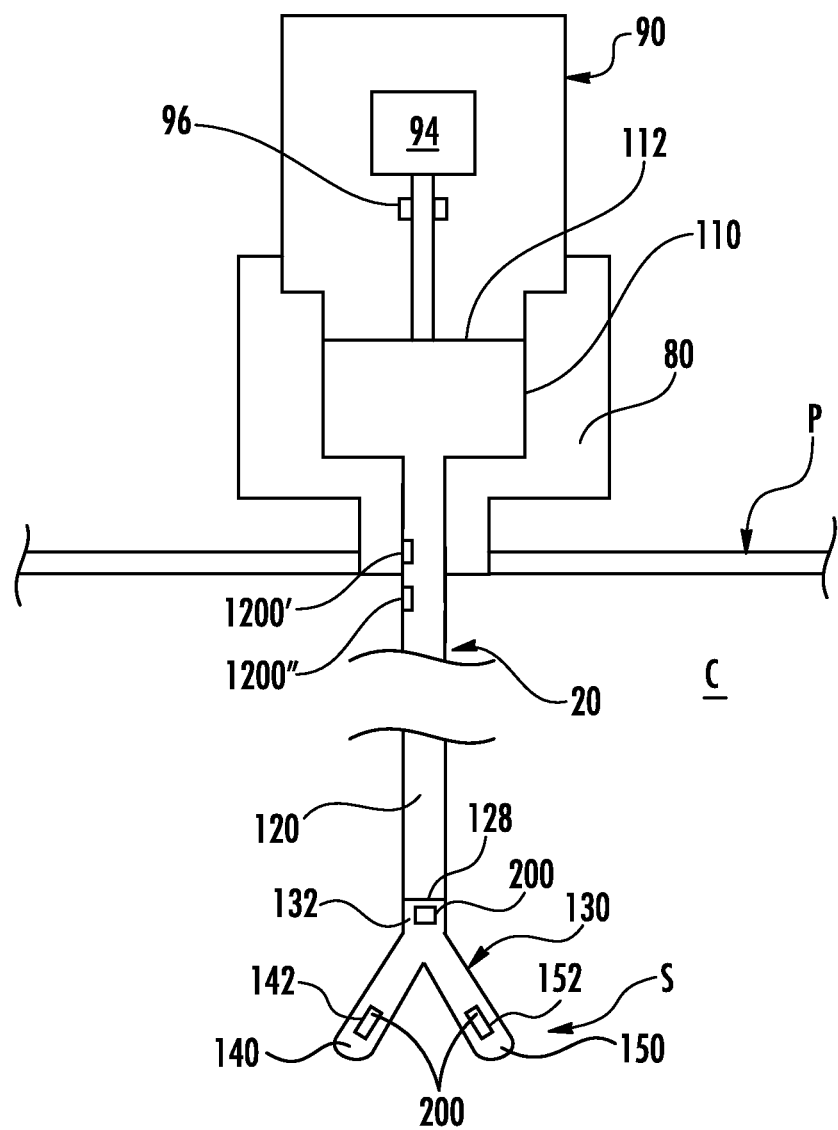
FIG. 2 is a schematic illustration of a surgical instrument of the robotic system inserted into a body cavity of a patient.

With reference to FIG. 2, an instrument 20 is inserted into a body cavity "C" of a patient "P" through a port or trocar 80 to access the surgical site "S". The instrument 20 includes a housing or body 110, an elongate shaft 120, and an end effector 130. The body 110 includes an interface 112 that couples to an instrument drive unit (IDU) 90 which provides mechanical energy or input for manipulating the instrument 20. The IDU 90 may also provide electrical and/or optical energy to the instrument 20 through the interface 112. In addition, the instrument 20 may provide feedback signals, electrical, mechanical, and/or optical, to IDU 90. The IDU 90 is in communication with the processing unit 30 (FIG. 1) to receive signals for manipulating the instrument 20 and to provide feedback signals from the instrument 20 and the IDU 90 to the processing unit 30 as described in detail below.

The elongate shaft 120 extends from the body 110 and is articulable in three degrees of freedom (DOF) relative to the body 110. It will be appreciated that the body 110 is moveable into and out of the trocar 80 to provide a fourth DOF. The body 110 includes an articulation mechanism (not explicitly shown) to articulate the elongate shaft 120 in response to mechanical input from the IDU 90.

The end effector 130 is supported at a distal end 128 of the elongate shaft 120 and includes a first jaw member 140 and a second jaw member 150 that are moveable relative to one another between an open position and a closed position. As shown, each of the first and second jaw members 140, 150 pivot relative to one another about a pin 134 (FIG. 3) of the end effector 130; however, one of the first or second jaw members 140, 150 may be fixed relative to the elongate shaft 120 with the other one of the first or second jaw members 140, 150 moveable relative to the fixed jaw member. The IDU 90 includes a motor 94 that is associated with the end effector 130 to transition the first and second jaw members 140, 150 between the open and closed positions. Some IDUs 90 may include two or more motors 94 that may actuate one or more features of instrument 20. One or more of the motors 94 may be associated with respective cables to actuate one or more features of the instrument 20. These features may include, for example, articulation of the jaws 140, 150 or end effector 130 in one or more degrees of freedom. As detailed below, the IDU 90 includes a torque or force sensor 96 that generates a direction signal indicative of whether the motor 94 is transitioning the first and second jaw members 140, 150 towards the closed position or towards the open position.

Figure 3:
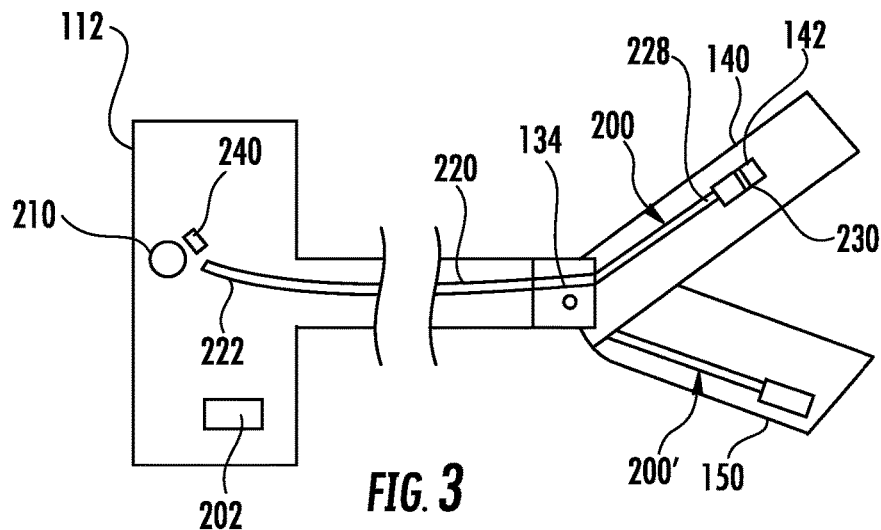
FIG. 3 is a schematic illustration of an optical force sensor of the surgical instrument of FIG. 2 provided in accordance with the present disclosure.
Figure 4:
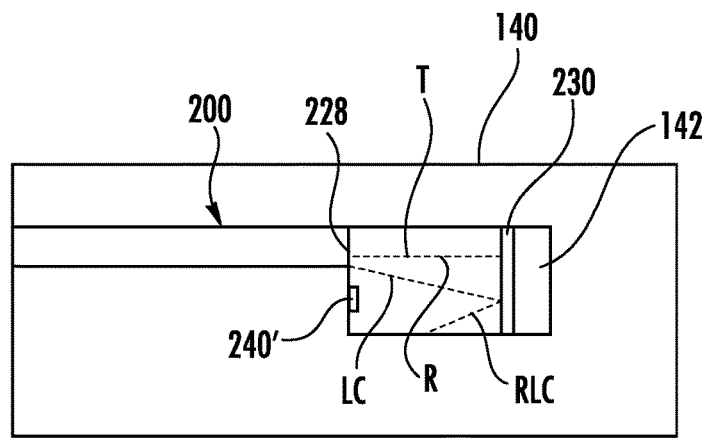
FIG. 4 is a schematic illustration of the first jaw member of the surgical instrument of FIG. 2 including the optical force sensor of FIG. 3 in a neutral configuration.

Referring to FIGS. 3 and 4, the first jaw member 140 defines a cavity 142 that includes an optical force sensor 200 in accordance with the present disclosure. The optical force sensor 200 includes a light source 210, a light guide 220, a reflector 230, and a light receiver 240. As shown, the light source 210 is disposed in the body 110 (FIG. 2); however, it is contemplated that the light source 210 (e.g., a microLED or laser diode) may be disposed in the elongate shaft 120 or the end effector 130 (e.g., a yoke 132 of the end effector 130 or the first or second jaw member 140, 150). The light guide 220 may be in the form of an optical fiber (e.g., fiber optic cable) that extends from the body 110, through the elongate shaft 120, and into the end effector 130. The light guide 220 includes a proximal end 222 that is in optical communication with the light source 210 to receive light provided by the light source 210 and a distal end 228 disposed in the cavity 142 defined within the first jaw member 140.

The reflector 230 is supported by the first jaw member 140 within the cavity 142. The walls defining the cavity 142 may be treated with light absorbing material, a non-reflective material, or a diffusing material to increase the sensitivity of the optical force sensor 200. The reflector 230 is aligned with the distal end 228 of the light guide 220 such that light transmitted through the distal end 228 of the light guide 220 is in a light cone "LC" having a transmittance axis "T" that is directed towards the reflector 230. It will be appreciated that the amount of light at the transmittance axis "T" is greater than an amount of light at a point within the light cone "LC" a distance away (e.g., a radial distance) from the transmittance axis "T". The reflector 230 is a flat mirror that is disposed substantially orthogonal to the transmittance axis "T" such that light transmitted through the distal end 228 of the light guide 220 is reflected off of the reflector 230 back towards the distal end 228 of the light guide 220 in a reflected light cone "RLC" having a reflectance axis "R". It will be appreciated that an amount of light at the reflectance axis "R" is greater than an amount of light at a point within the reflected light cone "RLC" spaced apart (e.g., a radial distance) from the reflectance axis "R".

The light receiver 240 is disposed within the body 110 of the surgical instrument 100 in optical communication with the proximal end 222 of the light guide 220. The light receiver 240, which may in some instances be a photocell, may be configured to sense an amount of light reflected through the light guide 220 from the reflector 230.

It is contemplated that the reflector 230 may include a fluorescing material such that light emitted from the reflector 230 has a different wavelength than light striking the reflector 230. For example, the reflector 230 may be a scintillator mirror.

It is envisioned that the second jaw member 150 may also include an optical force sensor 200 disposed within a cavity 152 defined within the second jaw member 150. The optical force sensor 200 disposed within the second jaw member 150 may share the first light source 210 with the optical force sensor 200 disposed within the first jaw member 140. The optical force sensor 200 disposed within the second jaw member 150 functions in a similar manner to the optical force sensor 200 disposed within the first jaw member 140 as described below and will not be described in further detail herein.

Figure 5:
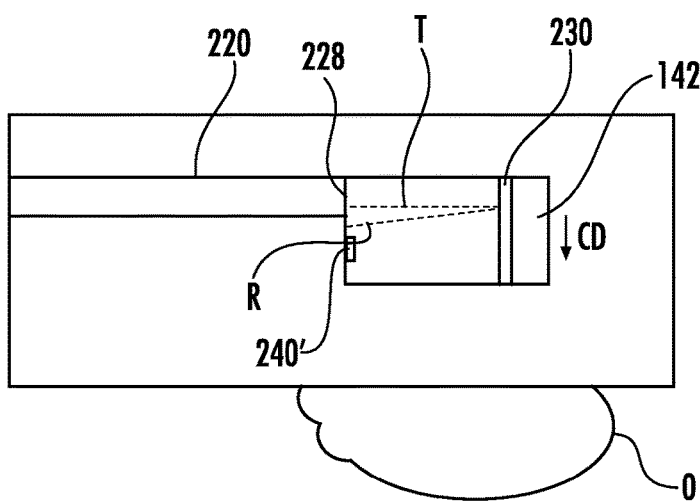
FIG. 5 is a schematic illustration of the optical force sensor of FIG. 4 in a closing configuration.
Figure 6:
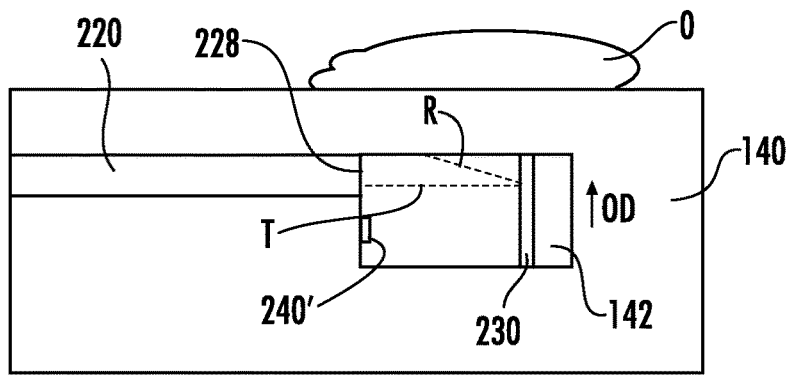
FIG. 6 is a schematic illustration of the optical force sensor of FIG. 4 in an opening configuration.

With reference to FIGS. 4-6, the first jaw member 140 has a rest or neutral configuration (FIG. 4), a clamping configuration (FIG. 5), and a distracting configuration (FIG. 6). In the neutral configuration, the first jaw member 140 is subject to little or no force (e.g., transverse force) such that the reflectance axis "R" is substantially aligned with the transmittance axis "T". The most amount of light may be reflected back to the light receiver 240 when the reflectance axis "R" is aligned with the transmittance axis "T".

In the clamping configuration, the first and second jaw members 140, 150 are moving towards the closed configuration. As shown in FIG. 5, the first jaw member 140 is in the clamping configuration moving in a first or closing direction as represented by arrow "CD" in FIG. 5. In the clamping configuration, the first and second jaw members 140, 150 may engage an obstruction "0" (e.g., tissue, bone, vessel, another surgical instrument, etc.) such that the first jaw member 140 is deformed or deflected by a deflection force. The deflection of the first jaw member 140 moves the reflector 230 within the cavity 142 of the first jaw member 140 which misaligns the reflectance axis "R" from the transmittance axis "T". When the reflectance axis "R" is misaligned with the transmittance axis "T", the amount of light returned through the light guide 220, and thus sensed by the light receiver 240, is less than when the first jaw member 140 is in the neutral configuration (i.e., when the reflectance axis "R" is aligned with the transmittance axis "T"). The difference (e.g., reduction) in the amount of light received by the light receiver 240 from the neutral configuration is indicative of the deflection of the first jaw member 140. With the deflection of the first jaw member 140 from the neutral configuration known, the deflection force exerted by the first jaw member 140 on the obstruction "O" can be determined.

In the distracting configuration, the first and second jaw members 140, 150 are moving towards the open configuration. As shown in FIG. 6, with the first jaw member 140 in the distracting configuration, the first jaw member 140 moves in a second or opening direction as represented by arrow "OD" in FIG. 6. In the distracting configuration, the first jaw member 140 is engaged with an obstruction "O" (e.g., tissue, bone, vessel, another surgical instrument, etc.) on an outer surface of the first jaw member 140 such that the first jaw member 140 is deflected by a deflection force. The deflection of the first jaw member 140 moves the reflector 230 within the cavity 142 of the first jaw member 140 which misaligns the reflectance axis "R" from the transmittance axis "T" as the first jaw member 140. When the reflectance axis "R" is misaligned with the transmittance axis "T", the amount of light returned through the light guide 220, and thus sensed by the light receiver 240, is less than when the first jaw member 140 is in the neutral configuration (i.e., when the reflectance axis "R" is aligned with the transmittance axis "T"). The difference (e.g., reduction) in the amount of light received by the light receiver 240 from the neutral configuration is indicative of the deflection of the first jaw member 140. With the deflection of the first jaw member 140 from the neutral configuration known, the deflection force exerted by the first jaw member 140 on the obstruction "O" can be determined. It is contemplated that the first jaw member 140 may include cuts or reliefs (not explicitly shown) in the walls to promote deflection of the first jaw member 140 and/or to increase sensitivity of the optical force sensor 200.

The optical force sensor 200 may include a processor 202 (FIG. 3) that receives a signal from the light receiver 240 indicative of the amount of light received and correlates or calculates the amount of light received into a deflection force exerted by or on the first jaw member 140. The processor 202 may be calibrated at the time of manufacture to associate a change in an amount of light received by the light receiver 240 with a deflection force of the first jaw member 140. Additionally or alternatively, the processor 202 may be calibrated before or during a surgical procedure to compensate for changes in the jaw member 140 (e.g., a permanent deformation, obstructions in the cavity "C", or conditions at the light source 210 or the light receiver 240).

As detailed above, the difference between the amount of light received by the light receiver 240 in the neutral configuration and the amount of light received by the light receiver 240 when the first jaw member 140 is deflected, in either the clamping or distracting configuration, is reduced. To differentiate between the clamping configuration and the distracting configuration, the processor 202 or the processing unit 30 receives a direction signal from the torque sensor 96 of the motor 94 indicative of a direction of movement of the first jaw member 140 (i.e., towards the open position or towards the closed position) to determine the configuration of the first jaw member 140, and thus, the direction of the deflection of the first jaw member 140. The processor 202 or the processing unit 30 may utilize the direction signal to calculate the deflection force as the first jaw member 140 may deflect asymmetrically in response to a given deflection force.

In aspects, the optical force sensor 200 may include a light receiver 240' disposed within the cavity 142 of the first jaw member 140 that sends a signal to the processor 202 indicative of an amount of light received by the light receiver 240'. The light receiver 240' is offset from the reflectance axis "R" and is disposed within a reflected light cone "RLC" of light transmitted through the distal end 228 of the light guide 220 and reflected off of the reflector 230. As shown in FIG. 5, when the first jaw member 140 is in the clamping configuration, the light receiver 240' receives an amount of light less than an amount of light received in the neutral configuration. When the first jaw member 140 is in the distracting configuration, the light receiver 240' receives an amount of light greater than an amount of light received in the neutral configuration as shown in FIG. 6. By offsetting the light receiver 240' from the reflectance axis "R" in the neutral configuration, the direction of the deflection of the first jaw member 140 and, thus, the direction of the force exerted by or on the first jaw member 140 can be determined from the increase or decrease in the amount of light received by the light receiver 240. Thus, the extent and the direction of the deflection force can be determined without the need for a direction signal from the torque sensor 96. It will be appreciated that by placing the light receiver 240' within the cavity 142, light may be continually transmitted through the distal end 228 of the light guide 220 without interfering with light reflected off of the reflector 230 to the light receiver 240 through the light guide 220.

In some aspects, the light receiver 240' may be used in conjunction with the light receiver 240 to provide a direction signal to the processor 202 and/or provide a verification of the extent of the deflection force.

Figure 7A:
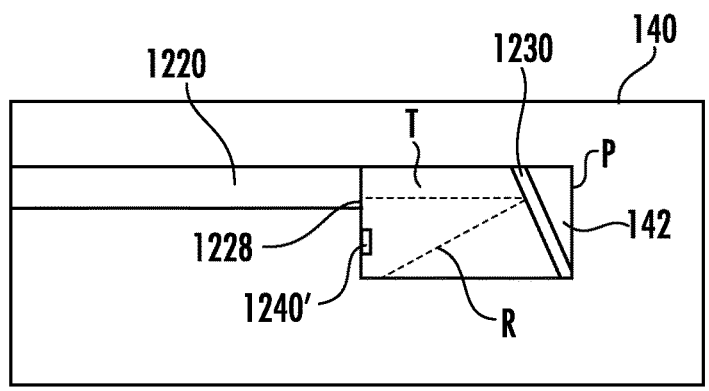
FIG. 7A is a schematic illustration of the first jaw member of the surgical instrument of FIG. 2 including another optical force sensor provided in accordance with the present disclosure in a neutral configuration.
Figure 7B:
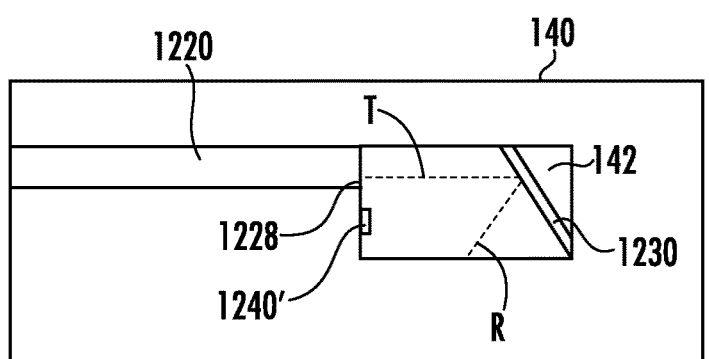
FIG. 7B is a schematic illustration of the optical force sensor of FIG. 7A in a closing configuration.
Figure 7C:
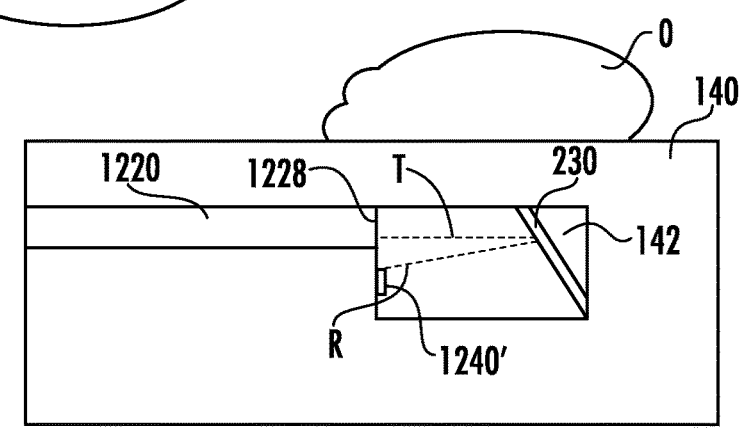
FIG. 7C is a schematic illustration of the optical force sensor of FIG. 7A in an opening configuration.

Referring now to FIGS. 7A-C, another optical force sensor 1200 is provided in accordance with the present disclosure. The optical force sensor 1200 is similar to the optical force sensor 200, as such, only the differences will be detailed below with like structures represented with a similar label including a "1" preceding the previous label.

The optical force sensor 1200 includes a light source 1210, a light guide 1220, a reflector 1230, and a light receiver 1240. The reflector 1230 is supported within the cavity 142 of the first jaw member 140 at an angle offset from a plane "P" orthogonal to the distal end 1228 of the light guide 1220 in the neutral configuration of the first jaw member 140. The angle may be in a range of about 5° to about 85° (e.g., about 15°). In the neutral configuration of the first jaw member 140, the reflectance axis "R" is offset from the transmittance axis "T" with the distal end 1228 of the light guide 1220 within the reflected light cone "RLC" of light transmitted through the distal end 1228 of the light guide 1220.

In use, when the first jaw member 140 is in the neutral configuration, an amount of light is reflected into the distal end 1228 of the light guide 1220 which is transmitted through the light guide 1220 and onto the light receiver 1240. The amount of light transmitted onto the light receiver 1240 is measured by the light receiver 1240. When the first jaw member 140 is in the clamping configuration, as shown in FIG. 7B, an amount of light is reflected off of the reflector 1230 into the distal end 1228 of the light guide 1220, and thus onto the light receiver 1240, is less than the amount of light reflected into the distal end 1228 when the first jaw member 140 is in the neutral configuration. When the first jaw member 140 is in the dissecting configuration as shown in FIG. 7C, an amount of light reflected into the distal end 1228 of the light guide 1220, and thus onto the light receiver 1240, is greater than the amount of light reflected into the distal end 1228 when the first jaw member 140 is in the neutral configuration.

As detailed above, by disposing the reflector 1230 within the cavity 142 of the first jaw member 140, at an angle relative to the distal end 1228 of the light guide 1220, such that the reflectance axis "R" is offset from the transmittance axis "T", when the first jaw member 140 is in the neutral configuration, the optical force sensor 1200 senses the extent and direction of the deflection of the first jaw member 140.

In aspects, the optical force sensor 1200 includes a light receiver 1240' disposed within the cavity 142 of the first jaw member 140 that sends a signal to a processor 1202 of the optical force sensor 1200 indicative of an amount of light received by the light receiver 1240'. The light receiver 1240' is offset from the reflectance axis "R" and is disposed within a reflected light cone "RLC". As shown in FIG. 7B, when the first jaw member 140 is in the clamping configuration, the light receiver 1240' receives an amount of light less than an amount of light received in the neutral configuration. When the first jaw member 140 is in the distracting configuration, the light receiver 1240' receives an amount of light greater than an amount of light received in the neutral configuration as shown in FIG. 7C. By offsetting the light receiver 1240' from the reflectance axis "R", the extent and the direction of the deflection of the first jaw member 140 is determined by the amount of light measured by the light receiver 1240'.

In some aspects, the light receiver 1240' is disposed within the cavity 142 and is aligned with the reflectance axis "R" when the first jaw member 140 is in the neutral configuration. Similar to the optical force sensor 200 detailed above, when the light receiver 1240' is aligned with the reflectance axis "R", when the first jaw member 140 is in either the clamping or distracting configurations, the amount of light received by the light receiver 1240' is less than when the first jaw member 140 is in the neutral configuration. In such aspects, the optical force sensor 1200 includes a processor 1202 that receives a direction signal from a torque sensor 96 (FIG. 2) associated with the motor 92 to determine the direction of the deflection of the first jaw member 140.

It is contemplated that the optical force sensor 1200 may utilize the light receiver 1240 to determine the direction of the deflection of the first jaw member 140 and the light receiver 1240' to determine the extent of the deflection of the first jaw member 140. Alternatively, the optical force sensor 1200 may utilize the light receiver 1240 to determine the direction and the extent of the deflection of the first jaw member 140 and utilize the light receiver 1240' to verify the extent of the deflection of the first jaw member 140.

Figure 8A:
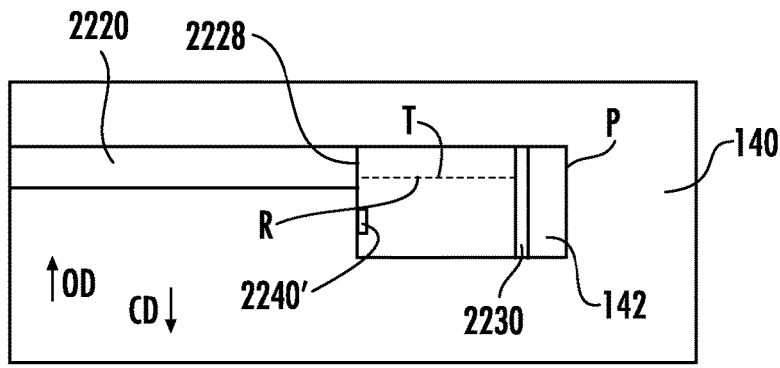
FIG. 8A is a schematic illustration of the first jaw member of the surgical instrument of FIG. 2 including another optical force sensor provided in accordance with the present disclosure in a neutral configuration.
Figure 8B:
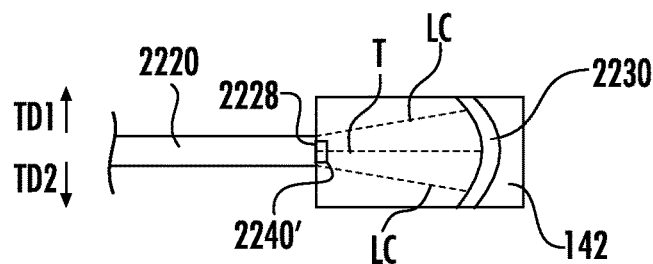
FIG. 8B is a top view of a cavity of the first jaw member of FIG. 8A.

Referring to FIGS. 8A-B, another optical force sensor 2200 is provided in accordance with the present disclosure. The optical force sensor 2200 is similar to the optical force sensor 200, as such, only the differences will be detailed below with like structures represented with a similar label including a "2" preceding the previous label.

The optical force sensor 2200 includes a light source 2210, a light guide 2220, a reflector 2230, and a light receiver 2240. The reflector 2230 is supported within the cavity 142 of the first jaw member aligned with the plane "P" orthogonal to a distal end 2228 of the light guide 2220. The reflector 2230 is concave in a first direction and flat in a second direction aligned with the opening and closing directions "OD", "CD" which is orthogonal to the first direction. The concavity of the reflector 2230 focuses light transmitted through the distal end 2228 of the light guide 2220 on the distal end 2228 of the light guide 2220 in a direction substantially parallel to the opening and closing directions "OD", "CD". As such, the reflected light cone "RLC" is substantially linear at the distal end 2228 of the light guide 2220 in a direction substantially parallel to the opening and closing directions "OD", "CD".

In use, the optical force sensor 2220 functions in a manner similar to the optical force sensor 200 for detecting deflection of the first jaw member 140 towards and away from the second jaw member 150 (i.e., in the opening direction "OD" or in closing direction "CD"). By reflecting light transmitted through the distal end 2228 of the light guide 2220 in a substantially linear reflected light cone "RLC", the concavity of the reflector 2230 isolates deflection of the first jaw member 140 in the opening and closing directions "OD", "CD" from deflection of the first jaw member 140 in a first transverse direction "TD1" or a second transverse direction "TD2". Thus, the concavity of the reflector 2230 may increase the accuracy of the optical force sensor 2220 for detecting an extent of the deflection of the first jaw member 140 in the opening and closing directions "OD", "CD". It is contemplated that the reflector 2230 concave in both the first and second directions such the reflector 2230 focuses light transmitted through the distal end 2228 of the light guide 2220 to a point or a focused spot.

In aspects, the optical force sensor 2200 includes a light receiver 2240' disposed within the cavity 142 of the first jaw member 140. The light receiver 2240' is positioned offset from a transmittance axis "T" of the light cone "LC" of light transmitted through the distal end 2228 of the light guide 2220 and aligned with the distal end 2228 of the light guide 2220 such that the light receiver 2240' receives a substantially linear reflected light cone "RLC". In use, the light receiver 2240' functions substantially similar to the light receiver 240' and may have increased accuracy for detecting an extent of the deflection of the first jaw member 140.

Figure 9A:
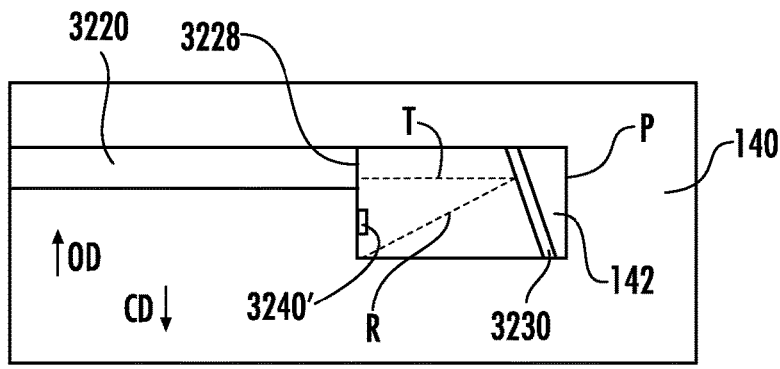
FIG. 9A is a schematic illustration of the first jaw member of the surgical instrument of FIG. 2 including another optical force sensor provided in accordance with the present disclosure in a neutral configuration.
Figure 9B:
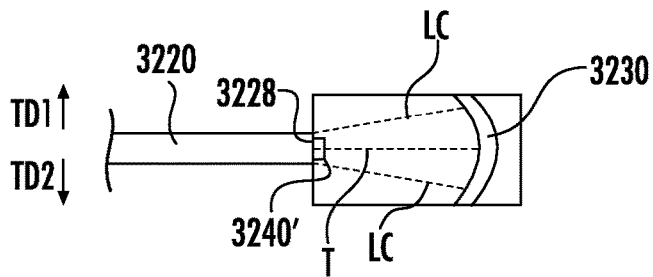
FIG. 9B is a top view of a cavity of the first jaw member of FIG. 9A.

Referring to FIGS. 9A and 9B, another optical force sensor 3200 is provided in accordance with the present disclosure. The optical force sensor 3200 is similar to the optical force sensor 1200, as such, only the differences will be detailed below with like structures represented with a similar label replacing the first numeral "1" with a numeral "3".

The optical force sensor 3200 includes a light source 3210, a light guide 3220, a reflector 3230, and a light receiver 3240. The reflector 3230 is supported within the cavity 142 of the first jaw member 140 at an angle offset from a plane "P" orthogonal to a distal end 3228 of the light guide 3220. The reflector 3230 is concave in a first direction and flat in a second direction aligned with the opening and closing directions "OD", "CD" which is orthogonal to the first direction. The concavity of the reflector 3230 focuses light transmitted through the distal end 3228 of the light guide 3220 on the distal end 3228 of the light guide 3220 in a direction substantially parallel to the opening and closing directions "OD", "CD". As such, the reflected light cone "RLC" is substantially linear at the distal end 3228 of the light guide 3220 in a direction substantially parallel to the opening and closing directions "OD", "CD".

In use, the optical force sensor 3220 functions in a manner similar to the optical force sensor 1200 for detecting deflection of the first jaw member 140 towards and away from the second jaw member 150 (i.e., in the opening direction "OD" or in closing direction "CD"). By reflecting light transmitted through the distal end 3228 of the light guide 3220 in a substantially linear reflected light cone "RLC", the concavity of the reflector 3230 isolates deflection of the first jaw member 140 in the opening and closing directions "OD", "CD" from deflection of the first jaw member 140 in a first transverse direction "TD1" or a second transverse direction "TD2". Thus, the concavity of the reflector 3230 may increase the accuracy of the optical force sensor 3220 for detecting an extent of the deflection of the first jaw member 140 in the opening and closing directions "OD", "CD".

In aspects, the optical force sensor 3200 includes a light receiver 3240' disposed within the cavity 142 of the first jaw member 140 that sends a signal to a processor 3202 of the optical force sensor 3200 indicative of an amount of light received by the light receiver 3240'. The light receiver 3240' is offset from the reflectance axis "R" and is disposed within a reflected light cone "RLC" of light transmitted through the distal end 3228 of the light guide 3220. When the first jaw member 140 is in the clamping configuration, the light receiver 3240' receives an amount of light less than an amount of light received in the neutral configuration. When the first jaw member 140 is in the distracting configuration, the light receiver 3240' receives an amount of light greater than an amount of light received in the neutral configuration. By offsetting the light receiver 3240' from the reflectance axis "R", the extent and the direction of the deflection of the first jaw member 140 is determined by the amount of light measured by the light receiver 3240'.

In some aspects, the light receiver 3240' is disposed within the cavity 142 and is aligned with the reflectance axis "R" when the first jaw member 140 is in the neutral configuration. Similar to the optical force sensor 200 detailed above when the light receiver 3240' is aligned with the reflectance axis "R", when the first jaw member 140 is in either the clamping or distracting configurations, the amount of light received by the light receiver 3240' is less than when the first jaw member 140 is in the neutral configuration. In such aspects, the optical force sensor 3200 includes a processor 3202 that receives a direction signal from a torque sensor 96 (FIG. 2) associated with the motor 92 to determine the direction of the deflection of the first jaw member 140.

Figure 10A:
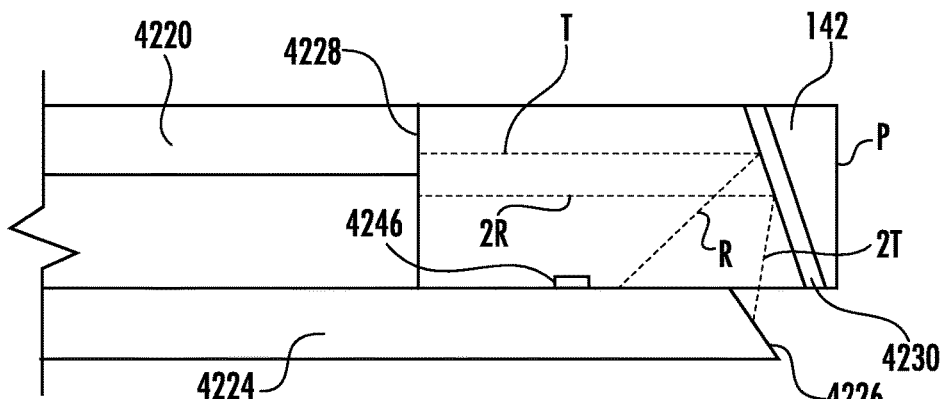
FIG. 10A is a schematic illustration of the first jaw member of the surgical instrument of FIG. 2 including another optical force sensor provided in accordance with the present disclosure in a neutral configuration.
Figure 10B:
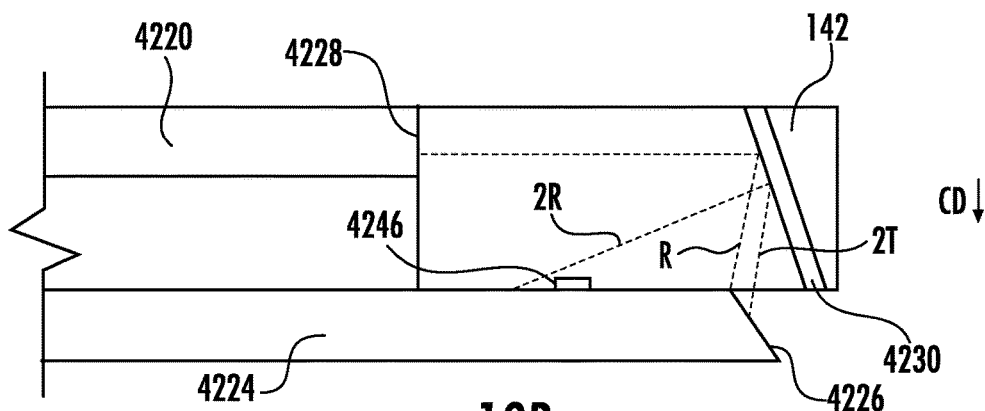
FIG. 10B is a schematic illustration of the optical force sensor of FIG. 7A in a closing configuration.
Figure 10C:
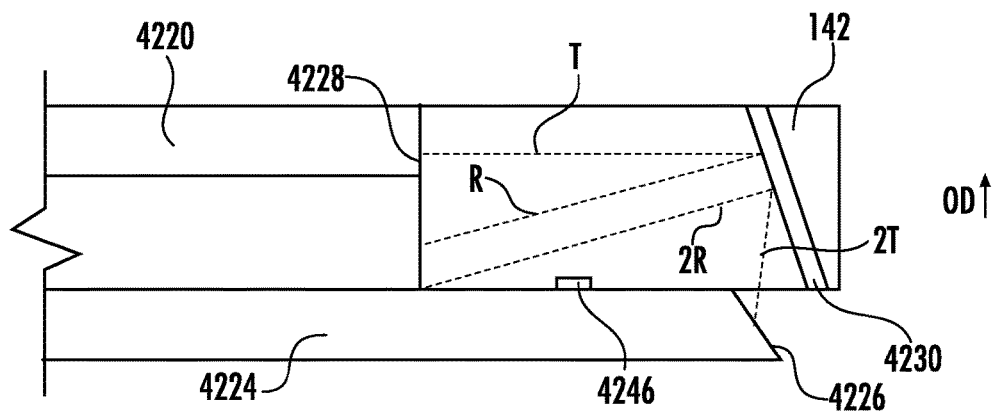
FIG. 10C is a schematic illustration of the optical force sensor of FIG. 7A in an opening configuration.

Referring now to FIGS. 10A-C, another optical force sensor 4200 is provided in accordance with the present disclosure. The optical force sensor 4200 is similar to the optical force sensor 200, as such, only the differences will be detailed below with like structures represented with a similar label including a "4" preceding the previous label.

The optical force sensor 4200 includes a first light source, a second light source, a first light guide 4220, a second light guide 4224, a reflector 4230, and a light receiver 4246. The reflector 4230 is supported within the cavity 142 of the first jaw member 140 at an angle offset from the plane "P" that is orthogonal to the distal end 4228 of the first light guide 4230.

In use, the first light source, the first light guide 4220, and the light receiver 4246 function in a similar manner to the similar components of the optical force sensor 1200 detailed above. As such, only the differences will be described below for reasons of brevity.

The second light source may be positioned within the body 110 (FIG. 2); however, it is contemplated that the second light source may be disposed in the elongate shaft 120 or the end effector 130 (e.g., the first or second jaw member 140, 150). The second light guide 4224 may be in the form of an optical fiber (e.g., fiber optic cable) that extends from the body 110, through the elongate shaft 120, and into the end effector 130. The second light guide 4224 includes a proximal end 4225 that is in optical communication with the second light source to receive light provided by the second light source and a distal end 4226 disposed in the cavity 142 defined within the first jaw member 140. The distal end 4226 of the second light guide 4224 is shaped such that light transmitted through the distal end 4226 defines a second transmittance axis "2T" orthogonal to the transmittance axis "T" of light transmitted through a distal end 4228 of a first light guide 4220. As shown, the distal end 4226 of the second light guide 4224 is disposed at about a 45° angle to transmit a light cone "LC" towards the reflector 4230; however, the second light guide 4224 may curve adjacent the distal end 4226 such that the distal end 4226 is flat, similar to the distal end 4228 of the first light guide 4220. The distal end 4226 of the second light guide 4224 is positioned offset from the reflectance axis "2R" of light transmitted through the distal end 4226. Light received at the distal end 4226 of the second light guide 4224 is transmitted through the second light guide 4224 to the light receiver 4246. The light receiver 4246 may be disposed within the body 110 of the surgical instrument 100 and is configured to sense an amount of light reflected from the reflector 4230 and returned through the second light guide 4224.

The first and second light sources may produce light having properties different from one another such that the light transmitted from one of the first and second light sources and ultimately reflected from the light reflector 4230 may be differentiated from light produced by the other one of the first and second light sources. For example, the light sources may be time or frequency modulated to differentiate the light from each source. Other differentiation techniques may also be used. In some instances the light sources may be selected to emit a specific wavelength of light in a range of about $10^{16}$ m to about 1 m in length. The light receiver 4246 may be configured detect the differentiated light emitted from each of the light sources so that the amount of light reflected to the receiver 4246 from each of the sources may be measured.

In aspects, the distal end 4228 of the first light guide 4220 is offset from the reflectance axis "R" and within the reflected light cone "RLC" of light transmitted through the distal end 4226 of the second light guide 4224. Similarly, the distal end 4226 of the second light guide 4224 is offset from the reflectance axis "R", and is within the reflected light cone "RLC" of light transmitted through the distal end 4228 of the first light guide 4220. The light receiver 4246 may be positioned in optical communication with a proximal end 4215 of the second light guide 4224 to measure an amount of light transmitted through the distal end 4228 of the first light guide 4220, reflected off of the reflector 4230, and into the distal end 4226 of the second light guide 4224. The amount of light measured by the light receiver 4246 is indicative of the deflection of the first jaw member 140 in the opening or closing direction "OD", "CD". The light receiver 4246 may also be positioned in optical communication with a proximal end 4222 of the first light guide 4220 to measure an amount of light transmitted through the distal end 4226 of the second light guide 4224, reflected off of the reflector 4230, and into the distal end 4228 of the first light guide 4220. By each of the first and second light sources producing light having different properties, the light sources can continuously produce light and the light receiver 4246 can continuously measure an amount of light from each of the light sources.

The first and second light signals are transmitted to a processor 4202 or the processing unit 30 (FIG. 1) which calculates the direction and extent of deflection of the first jaw 140. The processor 4202 or the processing unit 30 calculates deflection of the first jaw 140 in the opening or closing direction "OD", "CD" from the first light signal and calculates deflection of the first jaw 140 in the first or second transverse direction "1TD", "2TD" from the second light signal.

In some aspects, the optical force sensor 4200 includes third light receiver 4246 disposed within the cavity 142 of the first jaw member 140. The third light receiver 4246 is positioned between the distal end 4228 of the first light guide 4220 and the distal end 4226 of the second light guide 4224 offset from the reflectance axes "R", "2R" and within the reflected light cone "RLC" of light transmitted through the distal end 4228 of the first light guide 4220 and the distal end 4226 of the second light guide 4224, respectively. The light receiver 4246 may be configured to differentiate light produced by the first light source from light produced by the second light source such that the light receiver 4246 can measure an amount of light received that is produced by the first light source and an amount of light received that is produced by the second light source. The light receiver 4246 generates a first light signal indicative of the amount of light received that is produced by the first light source and a second light signal indicative of the amount of light received that is produced by the second light source.

In particular aspects, the distal end 4228 of the first light guide 4220 may be shaped such that the reflected light cone "RLC" of light transmitted through the distal end 4228 of the first light guide 4220 in the clamping, distracting, and neutral configurations does not contact the distal end 4226 of the second light guide 4224. Similarly, the distal end 4226 of the second light guide 4224 may be shaped such that the reflected light cone "RLC" of light transmitted through the distal end 4226 of the second light guide 4224 does not contact the distal end 4228 of the first light guide 4220 in response to deflection of the first jaw 140.

As detailed and shown above, the optical force sensors (i.e., optical force sensors 200, 1200, 2200, 3200, 4200) are associated with the first jaw member 140 of the end effector 130; however, it is contemplated, as mentioned above, that second jaw member 150 may also include an optical force sensor to determine a force exerted on or by the second jaw member 150 as represented by optical force sensor 200' as shown in FIG. 3. Additionally or alternatively, the instrument 20 may include an optical force sensor 200" in the yoke 132 of the end effector 130 to measure forces exerted on or by the yoke 132.

Briefly referring back to FIG. 2, a pair of optical force sensors 1200', 1200" may be disposed within the elongate shaft 120 of the instrument 20 to determine the force exerted between the elongate shaft 120 and the trocar 80. Specifically, an optical force sensor 1200' is disposed in a portion of the elongate shaft 120 disposed within the trocar 80 and optical force sensor 1200" is disposed in a portion of the elongate shaft 120 of the instrument 20 outside of the trocar 80. The difference between a force measured by the optical force sensor 1200' and a force measured by the optical force sensor 1200" is indicative of the force exerted between the elongate shaft 120 and the trocar 80.

Figure 11:
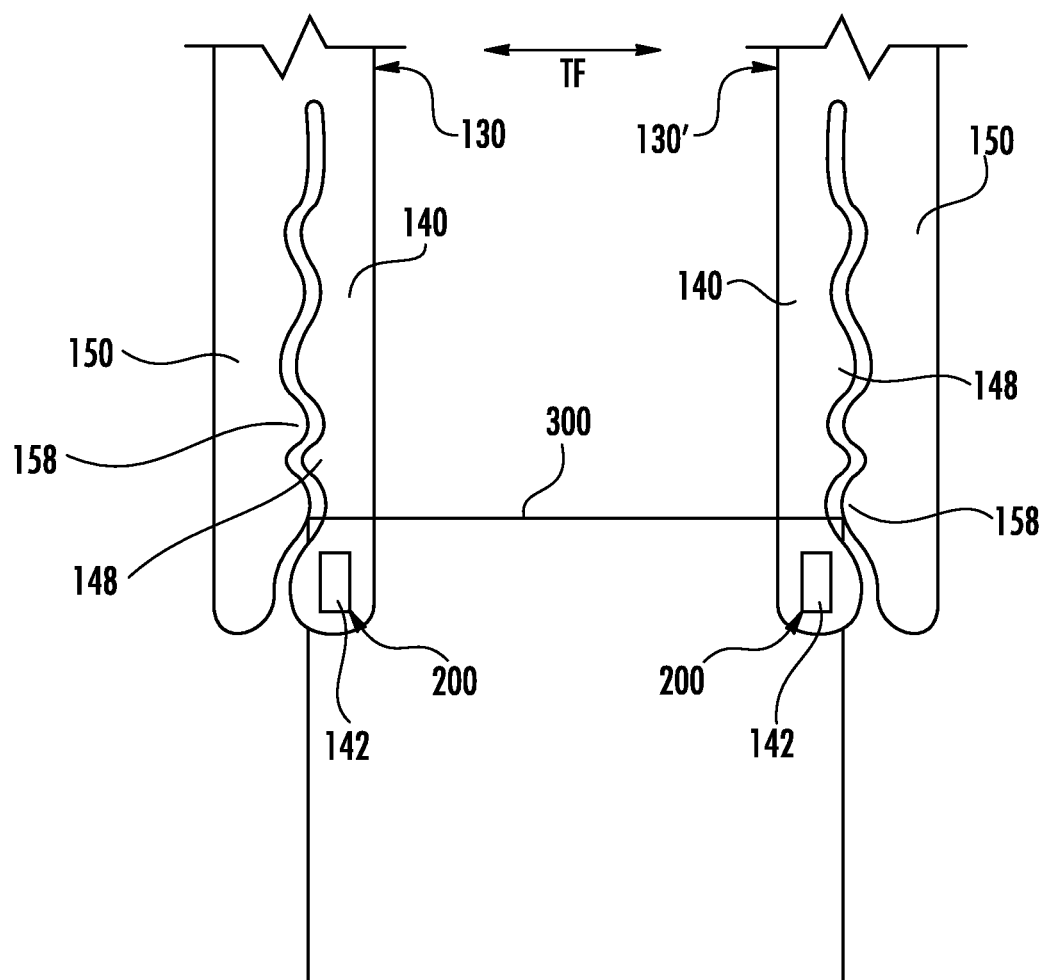
FIG. 11 is a side view of two end effectors of two surgical instruments each including an optical force sensor provided in accordance with the present disclosure.

Referring now to FIG. 11, a method of detecting suture slippage is described in accordance with the present disclosure. The method includes grasping a suture 300 with a first end effector 130 and a second end effector 130'. Each of the first and second end effectors 130, 130' has a first jaw member 140 and a second jaw member 150. Each first jaw member 140 includes an optical force sensor (e.g., optical force sensor 200, 1200, 2200, 3200, or 4200), as detailed above.

The suture 300 is grasped between the first jaw members 140 of the first and second end effectors 130, 130'. The first and second end effectors 130, 130' are in a closed position such that the second jaw member 150 of each of the first and second end effectors 130, 130' also engages the suture 300. Additionally or alternatively, the first jaw members 140 and/or the second jaw members may include grasping structures 148, 158 (e.g., teeth) that cooperate to engage the suture 300.

With the suture 300 grasped between the first jaw members 140 of the first and second end effectors 130, 130', the end effectors 130, 130' are drawn apart to apply a tension force "TF" to the suture 300.

To determine if the suture 300 is slipping with respect to one or both of the end effectors 130, 130', the force applied by each of the first jaw members 140 to the suture 300 is determined by the optical force sensor disposed in the first jaw members 140. The forces applied by each of the first jaw members 140 are summed together and compared to the tension force "TF" applied to the end effectors 130, 130'. If the sum of the forces applied by the first jaw members 140 is substantially equal to the tension force "TF" applied to the end effectors 130, 130', the suture 300 is not slipping relative to the end effectors 130, 130'. Alternatively, if the sum of the forces applied by the first jaw members 140 is less than the tension force "TF" applied to the end effectors 130, 130', the suture 300 is slipping relative to at least one of the end effectors 130, 130'. It will be appreciated, that the force applied to the suture by the first jaw members 140 may be the sum of forces applied in more than one axes (e.g., in the opening or closing direction and in the first or section transverse directions as detailed above) of the respective first jaw member 140.

By comparing the forces applied by each of the first jaw members 140, it may be determined which of the end effectors 130, 130' the suture 300 is slipping relative to. If the force applied by one of the first jaw members 140 is significantly less than the force applied by the other one of the first jaw members 140, the suture 300 is slipping relative to at least the first jaw member 140 applying the lower force to the suture 300. In response to the slippage of the suture 300, a closure force of the respective end effector 130, 130' may be increased to engage the suture 300 between the first and second jaw members 140, 150 of the respective end effector 130, 130' to prevent the slippage. The slippage of the suture 300 can then be redetermined as detailed above. The end effectors 130, 130' may be repositioned on the suture 300 before redetermining the slippage of the suture 300.

Figure 12:
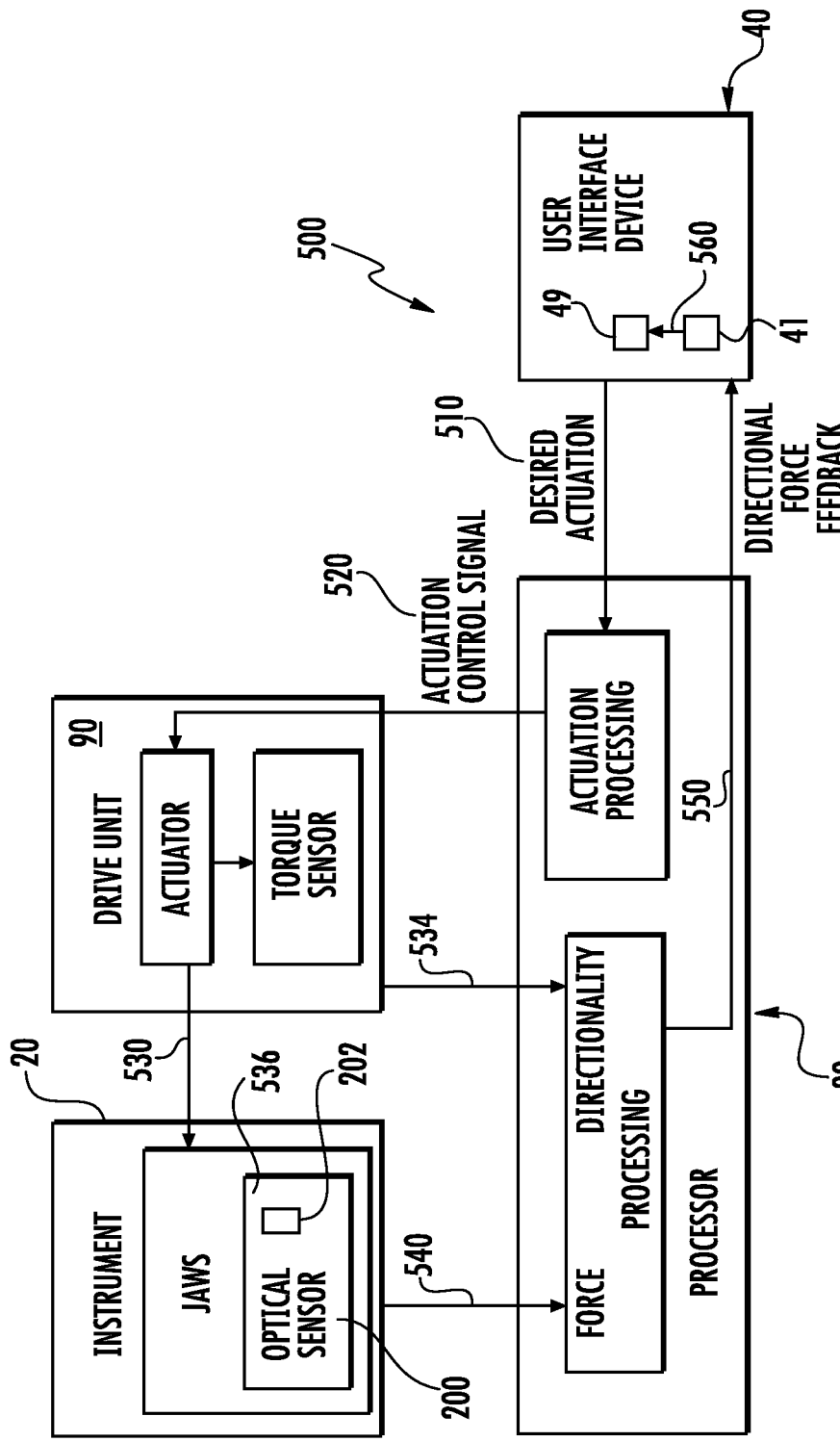
FIG. 12 is a flowchart illustrating a method of generating force feedback for a robotic surgical system in accordance with the present disclosure.

Referring to FIGS. 1 and 12, a method 500 for generating force feedback for a robotic surgical system is described in accordance with the present disclosure. Initially, a clinician engages an input device attached to a gimbal 70 of the user interface 40 to actuate an instrument 20 associated with the input device and the gimbal 70. To engage the input device, the clinician may move the input device, and thus the gimbal 70, or move a control (e.g., a button, a lever, an arm) of the input device. The input device and/or gimbal 70 generates and sends an actuation signal indicative of the actuation of the input device and/or gimbal 70 to the processing unit 30 (Step 510). The processing unit 30 analyzes the actuation signal and generates an actuation control signal which is transmitted to the IDU 90 associated with the instrument 20 (Step 520).

In response to the actuation control signal, the IDU 90 activates the motor 92 to actuate the instrument 20 (e.g., to actuate the end effector 130 to move the first and second jaw members 140, 150 towards the closed position) (Step 530). During actuation of the instrument 20, an optical force sensor disposed in one of the first or second jaw members 140, 150 (e.g., optical force sensor 200, 1200, 2200, 3200, 4200) is periodically or continuously measuring the deflection of one of the first or second jaw members 140, 150 to determine the force exerted by one of the first or second jaw members 140, 150. The optical force sensor generates and transmits a force signal to the processing unit 30 in response to the measured deflection of one of the first or second jaw members 140, 150 (Step 540). In response to the force signal, the processing unit 30 generates and transmits a feedback signal to a feedback controller 41 of the user interface 40 (Step 550). In response to the feedback signal, the feedback controller 41 activates a feedback motor 49 to provide feedback to the clinician engaged with the input device (Step 560).

As detailed above, the optical force sensor generates a force signal including an extent and a direction of the force exerted by one of the first or second jaw members 140, 150. When the optical force sensor generates a force signal that is only indicative of the extent of the force exerted by one of the first or second jaw members 140, 150 (e.g., when the optical force sensor is optical force sensor 200), the processing unit 30 receives a direction signal from the torque sensor 96 associated with the motor 92 (Step 534). The processing unit 30 receives and analyzes both the force signal and the direction signal to generate the feedback signal. Alternatively, the direction signal may be transmitted to a processor 202 of the optical force sensor (Step 536) which combines the direction signal with the extent of the deflection of one of the first or second jaw members 140, 150 to generate the force signal (Step 540).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical instrument comprising:
   a housing;
   an elongate shaft extending from the housing;
   a tool assembly supported by a distal portion of the elongate shaft, the tool assembly including first and second jaw member, at least one of the first and second jaw members moveable relative to the other jaw member between:
      a neutral configuration in which the first and second jaw members are spaced apart relative to one another; and
      a clamping configuration in which the first and second jaw members are approximated relative to one another with tissue grasped therebetween, the first jaw member defining a cavity; and
   an optical force sensor configured to determine a force exerted to tissue, the optical force sensor including:
      a light source;
      a reflector disposed within the cavity of the first jaw member and configured to reflect light emitted from the light source;
      a light receiver configured to sense an amount of light reflected from the light source; and
      a processor in communication with the light receiver and configured to determine deflection of the first jaw member from the amount of sensed light, the deflection of the first jaw member correlated to a force exerted by the first jaw member to tissue.

2. The surgical instrument according to claim 1, wherein the light source is disposed within the housing.

3. The surgical instrument according to claim 2, wherein the optical force sensor includes a light guide extending between the light source and the cavity.

4. The surgical instrument according to claim 3, wherein the light receiver is disposed within the housing and in communication with the light guide such that light reflected from the reflector passes through the light guide.

5. The surgical instrument according to claim 4, wherein light reflected from the reflector has at least one property different than light emitted towards the reflector, the at least one property is at least one of a phase or a wavelength.

6. The surgical instrument according to claim 1, wherein the light receiver is disposed within the cavity.

7. The surgical instrument according to claim 6, wherein the first jaw member has a tissue contacting surface opposing the second jaw member and an outer surface opposite the tissue contacting surface, the first and second jaw members have a distracting configuration in which the outer surface of the first jaw member is engaged with tissue.

8. The surgical instrument according to claim 7, wherein in the clamping configuration the first jaw member is deflected in a first direction and in the distracting configuration the first jaw member is deflected in a second direction opposite the first direction, the processor being configured to determine a direction of deflection of the first jaw member from the amount of light received by the light receiver.

9. The surgical instrument according to claim 1, wherein the reflector is disposed orthogonal to an axis of transmittance of light emitted from the light emitter.

10. The surgical instrument according to claim 1, wherein the reflector is disposed at an angle relative to an axis of transmittance of the light emitted from the light emitter in a range of about 5° to about 85°.

11. The surgical instrument according to claim 1, wherein the reflector is concave.

12. The surgical instrument according to claim 11, wherein the concavity of the reflector is configured to direct the entire amount of light emitted from the light source towards the light detector when the first jaw member is in the neutral configuration.

13. The surgical instrument according to claim 1, wherein the light source is at least one of a microLED or a laser diode.

14. A tool assembly comprising:
a jaw member defining a cavity;
an optical force sensor configured to determine a force exerted to tissue by a jaw tool assembly, the tool assembly defining a cavity, the optical force sensor including:
a first light source;
a reflector disposed within a cavity of the tool assembly and configured to reflect light emitted from the first light source;
a light receiver configured to sense an amount of emitted by the first light source and reflected by the reflector; and
a processor in communication with the light receiver and configured to determine deflection of the first jaw member from the amount of sensed light, the deflection of the first jaw member correlated to a force exerted by the first jaw member to tissue.

15. The tool assembly according to claim 14, wherein the optical force sensor includes a second light source, the reflector configured to reflect light emitted from the second light source, the light receiver configured to sense an amount of light emitted by the second light source and reflected by the reflector.

16. The tool assembly according to claim 15, wherein the cavity is defined by a first sidewall and a second sidewall perpendicular to the first sidewall, the first light source configured to emit light through an opening in the first sidewall and the second light source configured to emit light through an opening in the second sidewall.

17. The tool assembly according to claim 15, wherein the first light source is configured to emit light having a first property and the second light source is configured to emit light having a second property different from the first property, the light detector differentiating between sensed light from the first light source and sensed light from the second light source.

18. A method of determining a force applied to tissue by a jaw member of a tool assembly, the method comprising:
engaging tissue with a jaw member of a tool assembly such that the jaw member is deflected;
emitting light from a light source towards a reflector disposed within a cavity defined in within the jaw member;
sensing an amount of light from the first light source reflected by the reflector with a light detector; and
determining the force applied to the tissue by the jaw member from the amount of sensed light.

19. The method according to claim 18, wherein engaging tissue with the jaw member includes at least one of engaging tissue with a tissue contacting surface of the jaw member in a clamping configuration or engaging tissue with an outside surface of the jaw member opposite the tissue contacting surface in a distracting configuration.

20. The method according to claim 18, wherein determining the force applied to tissue by the jaw member includes a configuration of the jaw member based on the amount of sensed light.

* * * * *